(12) United States Patent
Fojtik

(10) Patent No.: US 9,364,641 B2
(45) Date of Patent: Jun. 14, 2016

(54) ELONGATE MEDICAL INSTRUMENTS WITH REMOVABLE CORE GUIDE WIRE EXTENDERS, GUIDE WIRE EXTENDERS, SYSTEMS AND METHODS

(75) Inventor: Shawn P. Fojtik, Park City, UT (US)

(73) Assignee: Control Medical Technology, LLC, Park City, UT (US)

( * ) Notice: Subject to any disclaimer, the term of this patent is extended or adjusted under 35 U.S.C. 154(b) by 0 days.

(21) Appl. No.: 13/276,246

(22) Filed: Oct. 18, 2011

(65) Prior Publication Data

US 2012/0179111 A1  Jul. 12, 2012

Related U.S. Application Data

(63) Continuation-in-part of application No. 12/986,165, filed on Jan. 6, 2011, now abandoned.

(51) Int. Cl.
*A61M 25/09* (2006.01)
*A61M 25/01* (2006.01)

(52) U.S. Cl.
CPC ........... *A61M 25/0905* (2013.01); *A61M 25/01* (2013.01)

(58) Field of Classification Search
CPC ............ A61M 25/01; A61M 25/0169; A61M 25/09041; A61M 25/0905
USPC ................. 604/164.01, 164.13, 528; 600/585
See application file for complete search history.

(56) References Cited

U.S. PATENT DOCUMENTS

| | | | | |
|---|---|---|---|---|
| 4,594,073 A | * | 6/1986 | Stine | 604/187 |
| 4,958,642 A | * | 9/1990 | Christian et al. | 600/585 |
| 4,966,163 A | * | 10/1990 | Kraus et al. | 600/585 |
| 5,117,838 A | * | 6/1992 | Palmer et al. | 600/585 |
| 5,137,288 A | | 8/1992 | Starkey et al. | |
| 5,139,032 A | * | 8/1992 | Jahrmarkt et al. | 600/585 |
| 5,188,621 A | | 2/1993 | Samson | |
| 5,191,888 A | * | 3/1993 | Palmer et al. | 600/434 |
| 5,219,332 A | | 6/1993 | Nelson et al. | |
| 5,234,002 A | * | 8/1993 | Chan | 600/585 |
| 5,339,833 A | * | 8/1994 | Berthiaume et al. | 600/585 |
| 5,415,178 A | * | 5/1995 | Hsi et al. | 600/585 |

(Continued)

OTHER PUBLICATIONS

International Searching Authority—U.S. "International Search Report and Written Opinion" mailed May 1, 2012, in related PCT application No. PCT/US2012/020536.

*Primary Examiner* — Kami A Bosworth
(74) *Attorney, Agent, or Firm* — Durham Jones & Pinegar, P.C. Intellectual Property Law Group

(57) ABSTRACT

A guide wire extender includes a coupling element for coupling to a proximal portion of a guide wire. Such a configuration enables the introduction of elongate medical instruments that lack rapid exchange features to be introduced into the body of a subject over short, rapid exchange-length guide wires. Assemblies that include a guide wire extender within an elongate medical device are also disclosed. Such an assembly may include a configuration that enables a single user to effectively lengthen a guide wire and introduce the elongate medical instrument into a subject's body without significant risk of contaminating the elongate medical instrument. Systems that include a guide wire extender and an elongate medical instrument are also disclosed, as are methods of using the guide wire extender to introduce an elongate medical instrument into the body of a subject.

14 Claims, 4 Drawing Sheets

(56) References Cited

U.S. PATENT DOCUMENTS

| | | |
|---|---|---|
| 5,666,968 A | 9/1997 | Imran |
| 5,833,644 A * | 11/1998 | Zadno-Azizi et al. ........ 604/509 |
| 6,030,349 A | 2/2000 | Wilson et al. |
| 6,059,484 A | 5/2000 | Greive |
| 6,805,692 B2 | 10/2004 | Muni et al. |
| 7,513,878 B2 | 4/2009 | Hamilton |
| 2005/0148929 A1 * | 7/2005 | Gingles ..................... 604/95.04 |

* cited by examiner

ELONGATE MEDICAL INSTRUMENTS WITH REMOVABLE CORE GUIDE WIRE EXTENDERS, GUIDE WIRE EXTENDERS, SYSTEMS AND METHODS

CROSS-REFERENCE TO RELATED APPLICATION

This application is a continuation-in-part of U.S. patent application Ser. No. 12/986,165, filed on Jan. 6, 2011, and titled "ELONGATE MEDICAL INSTRUMENTS WITH REMOVEABLE CORE GUIDE WIRE EXTENDERS, GUIDE WIRE EXTENDERS, SYSTEMS AND METHODS," which is pending, the entire disclosure of which is, by this reference, hereby incorporated herein.

TECHNICAL FIELD

The present invention, in various embodiments, relates generally to apparatus and methods for effectively extending the lengths of guide wires. More specifically, the present invention relates to guide wire extenders, which may comprise catheters with removable core extension wires, and to other embodiments of guide wire extenders. The present invention also includes systems that include a guide wire, a guide wire extender with a distal end coupled to a proximal end of the guide wire, and an elongate medical instrument, such as to catheter that is initially provided over the guide wire extender.

BACKGROUND

Conventionally, guide wires had to be at least twice as long as the medical instrument (a catheter, etc.) they would guide into a subject's body. The total length of such a guide wire includes: a distal first portion that resides within the subject's body as the medical instrument is being introduced into the subject's body; a central second portion, which remains outside of the subject's body, for receiving the medical instrument prior to its introduction into the subject's body; and a proximal third portion that enables a healthcare provider to hold the guide wire in place as the medical instrument is being introduced into the subject's body.

Because of their lengths, and particularly due to the lengths of the portions of long guide wires that remain outside of a subject's body, long guide wires are occasionally contaminated, for example, by contacting the floor or some other contaminating surface. A contaminated guide wire may also contaminate a medical instrument it will guide into the body of a subject. Accordingly, when the exterior portion of a guide wire is contaminated before the guide wire has been used to introduce a medical instrument into the body of a subject, it must be replaced. Removal and replacement of a contaminated guide wire wastes money and time, and increases the risk of injury to the subject.

In an effort to avoid contamination of long guide wires, as well as the consequences of contamination, many health care professionals receive assistance from another individual. The use of additional manpower increases the cost of the procedure to the healthcare provider and, ultimately, to its patients.

The problems associated with contamination in many interventional procedures have been reduced by replacing long guide wires with so-called "rapid exchange," or "RX," solutions. Shorter guide wires may be used to introduce rapid exchange devices, such as RX catheters, into subjects' bodies. With shorter guide wires, the risk of contamination is reduced, as there is little likelihood that a shorter guide wire will contact a contaminating surface.

While rapid exchange technology works well under many circumstances, the features that enable rapid exchange consume valuable cross-sectional area and volume (e.g., in the form of diminished lumen sizes, etc.) within medical instruments. Thus, in situations where optimal cross-sectional areas and volumes are needed to provide optimal performance (e.g., in aspiration catheters, etc.), the use of rapid exchange features diminish the performance of a medical instrument.

Extendable guide wires have been developed to provide a short wire for certain applications (e.g., rapid exchange, etc.) and a longer wire for other situations. Conventionally, the only guide wires that could be extended are those that are configured for extension. Conventional extendable guide wires and their cooperating guide wire extenders typically include complementary engagement features that mate or otherwise cooperate with one another. Furthermore, the engagement features of conventional extendable guide wires are typically configured to couple to one another while maintaining the overall outer dimensions (e.g., outer diameter (OD), etc.) and shapes of the guide wires. These features render extendible guide wires quite a bit more expensive than conventional guide wires. Accordingly, health care professionals must anticipate situations where extendible guide wires will be needed, or unnecessarily increase the cost of procedures where they are not needed. Moreover, an extended guide wire is as prone to contamination as a conventional long guide wire.

SUMMARY

As used herein, a "guide wire" includes guide wires that are used to facilitate the introduction of catheters and other medical instruments to a desired location within the body of a subject, as well as other types of elongate wires with distal ends that are configured to be introduced and used within the body of a subject and proximal ends that are configured to remain outside of the subject's body during use.

According to one aspect, the present invention includes various embodiments of guide wire extenders. A guide wire extender of the present invention comprises an extension wire. The distal end of the extension wire is configured to couple to the proximal end of a guide wire, or is coupled to a coupling element for coupling to the proximal end of a guide wire. The distal end of an extension wire or a coupling element may be configured to couple with guide wires of a variety of different sizes (i.e., diameters or widths) and/or configurations. The distal end of a coupling element, an extension wire, a longer distal portion of the extension wire, or even the entire length of the extension wire may have a size that exceeds the size of any guide wire with which it may be coupled.

In various embodiments, the distal end of an extension wire or a coupling element configured to be secured to the distal end of an extension wire may be configured or include features for engaging the proximal end of a guide wire. Without limitation, such features may include tapering, the use of elastic materials, mechanical clamping elements, and the like. In some embodiments, a coupling element may comprise an elongated member with a receptacle extending through its length. A dimension across the receptacle (e.g., its diameter, etc.) may be smaller than a corresponding dimension of the proximal end of a guide wire (e.g. its diameter, etc.) that is to be secured to the coupling element. While this difference in dimensions, in conjunction with the use of an elastic material, may enable the coupling element to engage the proximal end of a guide wire, another feature or element may be useful for facilitating or enabling insertion of the proximal end of a guide wire into the receptacle of the coupling element. In a specific embodiment, an annular support may be located within a distal portion of the receptacle. A dimension across an opening through the annular support (e.g. its diameter, etc.) may be larger than a corresponding dimension of the guide wire (e.g., its diameter, etc). A tented or tapered region of the receptacle of the coupling element, adjacent to a proximal side of the annular support, may then receive the proximal end of the guide wire and guide it into a more constrictive portion of the receptacle.

A guide wire extender that incorporates teachings of the present invention may be provided in an assembled state with a medical instrument (e.g., an aspiration catheter, etc). When the guide wire extender includes such an assembly, an intermediate section of the extension wire (e.g., a majority of its length, etc) may reside within a lumen or other receptacle of the elongate medical instrument, while the distal and proximal ends of the extension wire may protrude from the respective distal and proximal ends of the elongate medical instrument. In some embodiments, the guide wire extender and its accompanying medical instrument may be provided to a user (e.g., a medical professional, etc.) in the assembled state, in which the guide wire extender comprises a removable core within the medical instrument.

The extension wire of the guide wire extender (along with any accompanying medical instrument when the guide wire extender comprises a removable core of the medical instrument) may be looped or coiled. The extension wire may be initially provided in a looped or coiled configuration, but have a more linear configuration when relaxed for example, when little or no tension or compression is applied to the extension wire. In embodiments where the extension wire of the guide wire extender forms the removable core of a medical instrument, a relaxed configuration of the medical instrument may define the initial shape of the extension wire.

Alternatively, the extension wire of a guide wire extender may be formed or shaped to remain in a looped or coiled configuration while the extension wire is in a relaxed state. The configuration of the extension wire may also define a configuration of an elongate medical instrument while the elongate medical instrument is installed upon the extension wire, or temporarily shape the elongate medical instrument.

A guide wire extender with an initial looped, coiled or similar configuration enables a single user, such as a health care professional, to couple the distal end of the extension wire to the proximal end of a guide wire without any significant risk that the proximal end of the extension wire or the proximal end of an elongate medical instrument installed upon the extension wire will be contaminated (e.g., by contacting the floor, etc.).

The present invention also includes systems. In various embodiments, a system of the present invention includes a guide wire, a guide wire extender and an elongate medical instrument. In some embodiments, the system may also include a connector (e.g., a Y adapter, a T adapter, etc.) coupled to a proximal end of the elongate medical instrument, with the guide wire and/or the guide wire extender, or a portion of the extension wire, extending through two arms of the connector. Such a connector enables a medical device to be coupled to the elongate medical instrument (e.g., an aspiration device in embodiments where the medical instrument comprises an aspiration catheter, etc.) while the distal end of the extension wire remains coupled to the proximal end of the guide wire.

In another aspect, the present invention includes methods for introducing elongate medical instruments into the body of as subject. In such as method, a guide wire is positioned within the body of the subject, with a proximal end of the guide wire located outside of the subject's body. A distal end of an extension wire is coupled to the proximal end of the guide wire. The elongate medical instrument, which may, in some embodiments, be pre-installed on the extension wire, may be moved proximally along the extension wire and the guide wire to introduce the elongate medical instrument into the body of the subject until a distal end of the elongate medical instrument reaches a desired location within the subject's body. A proximal end of the extension wire may be held in place during proximal movement of the elongate medical instrument. In some embodiments, the acts of coupling the distal end of the extension wire to the proximal end of the guide wire and introducing the elongate medical instrument into the body of the subject may all be effected by a single individual (e.g., health care professional, etc.).

Other aspects, along with features and advantages of various embodiments and aspects, of the present invention will become apparent to those of ordinary skill in the art through consideration of the ensuing description, the accompanying drawings and the appended claims.

BRIEF DESCRIPTION OF THE DRAWINGS

In the drawings:

FIG. 10 shows an assembly that includes a guide wire extender of the present invention and an elongate medical instrument with a small crossing profile;

DETAILED DESCRIPTION

The drawings illustrate embodiments of various aspects of the present invention.

Figure 1:
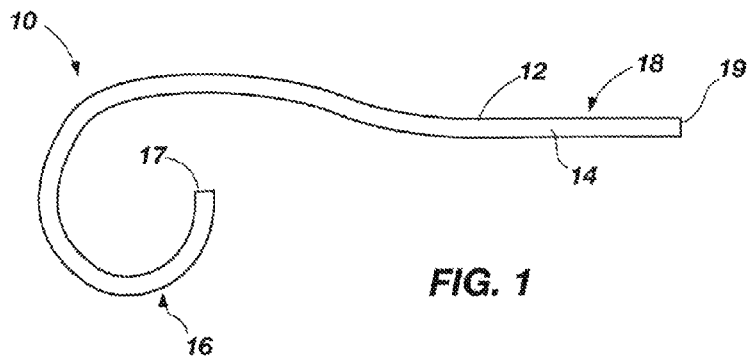
FIG. 1 illustrates a guide catheter.

In FIG. 1, an embodiment of a guide catheter 10 is depicted. In the depicted embodiment, the guide catheter 10 is configured to establish a path from a subject's leg to a left coronary artery of the subject's heart. Thus, the length and, optionally, the shape of the guide catheter enable the guide catheter to extend from a femoral artery within the subject's leg, through the descending aorta and the aortic arch, to (e.g., into or just proximal to) a coronary artery on the left side of the subject's heart.

Without limiting the scope of the present invention, a length of about 100 cm (i.e., about 1 m) enables the guide catheter 10 to extend from the subject's leg to a coronary artery on the left side of the subject's heart. A distal portion 16 of the guide catheter 10 may be shaped (e.g., curved, etc.) to reside within a subject's aortic arch and to position a distal end 17 proximate to or within, a coronary artery on the left side of the subject's heart. A proximal portion 18 of the guide catheter 10 may have a substantially linear configuration, enabling the proximal portion 18 to reside within and extend out one of the subject's femoral arteries and out of the subject's leg, with a proximal end 19 of the guide catheter 10 configured to reside outside of the subject's body.

In order to facilitate the introduction of one or more medical instruments in proximity to a coronary artery on the left side of the subject's heart, the guide catheter 10 may include a lumen 14 with a relatively large (e.g., 0.070 inch, etc.) inner diameter ID and a wall 12 with correspondingly sized (e.g., 0.080 inch, etc.) outer diameter OD.

Figure 2:
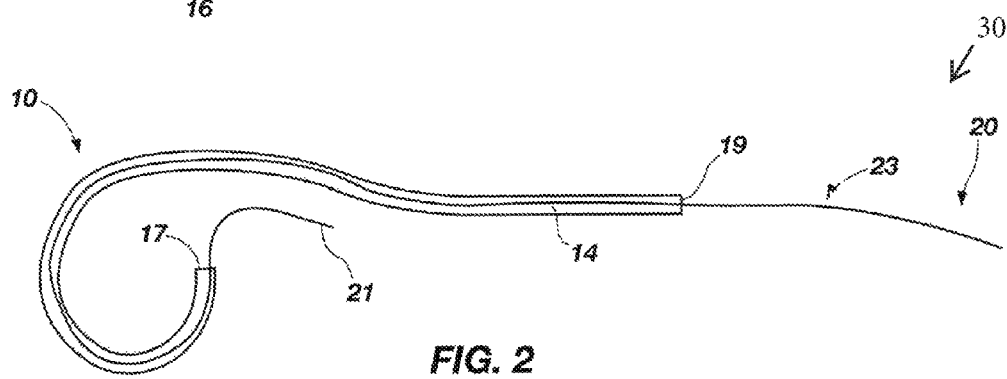
FIG. 2 depicts a short guide wire assembled with the guide catheter of FIG. 1.

FIG. 2 illustrates an embodiment of an assembly 30 that includes the guide catheter 10 shown in FIG. 1, as well as a guide wire 20 within a lumen 14 of the guide catheter 10. A length of the illustrated guide wire 20 exceeds a length of the guide catheter 10. Because of this difference in length, the guide wire 20 may extend through the entire length of the guide catheter 10. In addition, a distal end 21 of the guide wire 20 may protrude beyond the distal end 17 of the guide catheter 10. A proximal portion 23 of the guide wire 20 may also extend a sufficient distance beyond the proximal end 19 of the guide catheter 10 to enable a user to hold or manipulate the guide wire 20.

In a specific embodiment, a guide wire 20 that is configured filer use with a guide catheter 10, such as that described in reference to FIG. 1, may have a length of about 180 cm (i.e., about 1.8 m). When assembled with the guide catheter 10, the distal end 21 of the guide wire 20 may protrude about 20 cm beyond the distal end 17 of the guide catheter 10 (e.g., into a coronary artery on the left side of the subject' heart, etc.), while the proximal end 23 of the guide wire 20 may extend about 60 cm proximally beyond the proximal end 19 of the guide catheter 10, leaving 60 cm of wire for a user to hold or manipulate.

In some embodiments, the guide wire 20 may have an outer dimension OD or comparable dimension of about 0.014 inch.

Figure 3:
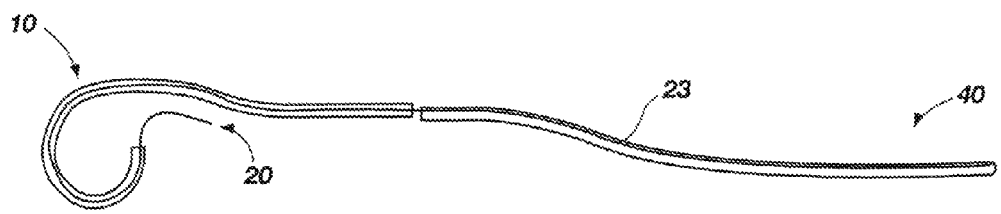
FIG. 3 shows the disparity in length between a portion of the short guide wire of FIG. 2 that remains outside of a subject' body and an elongate medical instrument.

Turning now to FIG. 3, an embodiment of an elongate medical instrument 40 is shown in association with the guide wire 20 described in reference to FIG. 2 and the guide catheter 10 described in reference to FIG. 1. As is non-limiting example, the elongate medical device 40 shown in FIG. 3 may comprise an aspiration catheter.

As shown, the elongate medical instrument 40 has a length (e.g., about 135 cm, etc.) that exceeds a length (e.g., about 60 cm) of the proximal portion 23 of the guide wire 20. Thus, when the elongate medical instrument 40 is introduced over the proximal portion 23 of the guide wire 20, none of the proximal portion 23 is available for a healthcare professional to retain.

Figure 4:
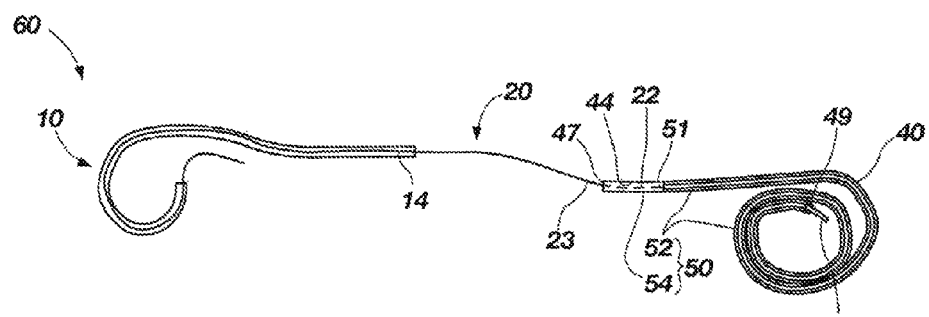
FIG. 4 depicts an embodiment of guide wire extender of the present invention, which may be used to enable introduction of the elongate medical instrument of FIG. 3 into the body of a subject over the short guide wire shown in FIGS. 2 and 3.

FIG. 4 illustrates an assembly 60 that includes an elongate medical instrument 40 and a guide wire extender 50.

While the elongate medical instrument 40 may comprise any suitable device, FIG. 4 depicts the elongate medical instrument 40 as being an aspiration catheter. The elongate medical instrument 40 may be configured for introduction into the lumen 14 of a guide catheter 10. In embodiments where the elongate medical instrument 40 comprises an aspiration catheter, a lumen 44 may extend through the entire length of the elongate medical instrument 40.

The guide wire extender 50 shown in FIG. 4 comprises an elongate extension 52 with a coupling element 54 at its distal end 51. The coupling element 54 may be secured to a distal end 51 of the elongate extension 52, or it may be formed integrally with the elongate extension 52.

The elongate extension 52 may also be referred to herein as an "extender wire" or, even more simply, as a "wire." Some embodiments of elongate extensions 52 have configurations similar to conventional guide wires; thus, such elongate extensions 52 may be manufactured from metals (e.g., surgical grade metals, etc.). In other embodiments, an elongate extension 52 may be fabricated from any suitable polymer (e.g., a polyether block amide (PEBA), such as that sold under the trade name PEBAX®; VESTIMED; a nylon, a heat shrink polymer, etc.) suitable for use in introducing elongate medical instruments into the body of a subject.

Similar materials may be used to form the coupling element 54 of the guide wire extender 50.

The coupling element 54 at the distal end of the elongate extension 52 of the guide wire extender 50 is configured to engage the proximal portion 23 of a guide wire 20, in a specific, but non-limiting embodiment, the coupling element 54 may include a receptacle for receiving and retaining, or coupling to, the proximal portion 23 of a guide wire 20. The receptacle of the coupling element 54 may include engagement features, such as a helical thread, ribs or other features configured to retain the proximal portion 23 of the guide wire 20 and prevent its separation from the coupling element 54.

The coupling element 54 may be configured to engage virtually any configuration of guide wire 20. Without limiting the scope of the present invention, a coupling element 54 may be configured to couple to (a) conventional guide wires 20 that have not otherwise been configured for extension; (b) guide wires 20 with features that enable coupling to a complementary extender; (c) guide wires 20 of a variety of different outer diameters (e.g. 0.014 inch guide wires, 0.014 inch ±0.002 inch guide wires, 0.010 inch guide wires, etc.); and/or (d) guide wires 20 of different cross-sectional shapes taken transverse to their lengths.

Figure 5:
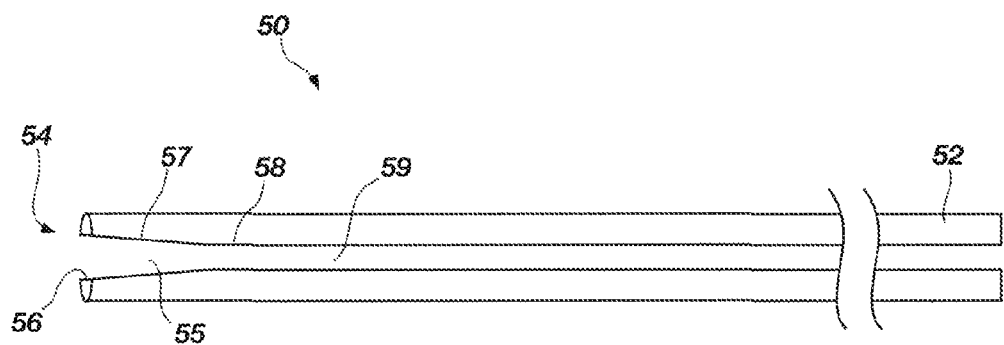
FIG. 5 illustrates an embodiment of a coupling element at the distal end of a guide wire extender of the present invention.

Referring now to FIG. 5, a specific, non-limiting embodiment of a coupling element 54 of a guide wire extender 50 is shown. The coupling element 54 includes a receptacle 55 for receiving a proximal end 22 of a guide wire 20 (see, e.g., FIG. 4). From its distal opening 56 to a more proximal location along the length of the coupling element 54, the receptacle 55 is tapered, having the shape of a truncated cone, or a funneled or frustoconical shape. In an even more specific embodiment, such a tapered portion 57 of the receptacle 55 may have an inner diameter of about 0.018 inch to about 0.035 inch (e.g., about 0.018 inch, about 0.020 inch, about 0.035 inch, etc.) at its distal opening 56 and an inner diameter of about 0.010 inch (e.g., 0.008 inch or less, etc.) at a proximal end 58. A tapered portion 57 of a receptacle 55 of a coupling element 54 may have any suitable length (e.g., about 5 cm, about 10 cm, about 20 cm, about 25 cm, etc.). The tapered portion 57 of a receptacle 55 may be configured to facilitate the reception of guide wires 20 of any of a variety of sizes and/or shapes.

The receptacle 55 of the coupling element 54 may also include a more proximally situated section of uniform or substantially uniform (e.g., accounting for manufacturing tolerances, etc.) cross-sectional shape and size. Such a uniform section 59 may be configured to retain the proximal portion 23 of as guide wire 20.

In some embodiments, including, but not limited to, those where the coupling element 54 is formed from a somewhat compressible, resilient material, the receptacle 55 may be configured to receive the proximal end 22 of a guide wire 20 (see, e.g., FIG. 4) and retain the proximal portion 2 of the guide wire 20 by compression or an interference fit. More specifically, as the proximal portion 23 of a guide wire 20 with particular dimensions (e.g., outer diameter, etc.) is forced into a portion of a receptacle 55 with smaller corresponding dimensions (e.g., inner diameter, etc.), the coupling element 54 may exert compressive forces on the proximal portion 23 of the guide wire 20. In embodiments of this type, a compression or interference it may be sufficient to prevent longitudinal movement of the coupling element 54 and, thus, the guide wire extender 50 relative to (e.g., off of etc.) the proximal end 22 of the guide wire 20.

In embodiments where the receptacle 55 of a coupling element 54 includes a tapered portion 57 and a uniform section 59, the tapered portion 57 of the receptacle 55 of a coupling element 54 may direct the proximal end 22 of a guide wire 20 into a uniform section 59 of the receptacle 55. When the coupling element 54 includes a compressible, resilient material, the tapered portion 57 may even direct the proximal end 22 of the guide wire 20 into a uniform section 59 with an inner diameter that is slightly smaller than the outer diameter of the proximal portion 23 of the guide wire 20.

Regardless of the shape and cross-sectional dimensions (e.g., inner diameter(s), etc.) of the receptacle 55 of a coupling element 54 of a guide wire extender 50 of the present invention, the receptacle 55 may be configured to receive a sufficient portion of the length of a guide wire 20 (see, e.g., FIG. 4) to ensure that the guide wire extender 50 remains coupled to the guide wire 20. Moreover, by inserting the guide wire 20 a sufficient distance into the receptacle 55 of the coupling element 54, kinking of the guide wire 20 may be prevented. In some embodiments, the receptacle of 55 may have a length of at least about 30 cm, at least about 40 cm, or more.

The dimensions (e.g., outer diameter, etc.) of the coupling element 54 and, optionally, a remainder of the guide wire extender 50 may exceed corresponding dimensions of the proximal portion 2 of a guide wire 20 to which the guide wire extender 50 is to be coupled. The difference in the dimensions of the guide wire 20 and the coupling element 54 enables a user to readily distinguish (e.g., see, feel, etc.) the guide wire 20 from the guide wire extender 50. In addition, by occupying more of the area within the lumen of an elongate medical instrument 40 than a standard guide wire 20, a larger guide wire extender 50 may prevent kinking of an elongate medical instrument 40 during its introduction into the body of a subject.

Figure 6B:
FIGS. 6A and 6B show an embodiment of guide wire extender with a coupling element that includes a clamp.
Figure 6A:
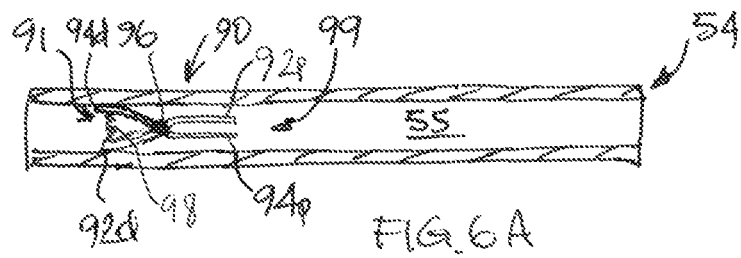
Figure 6B:
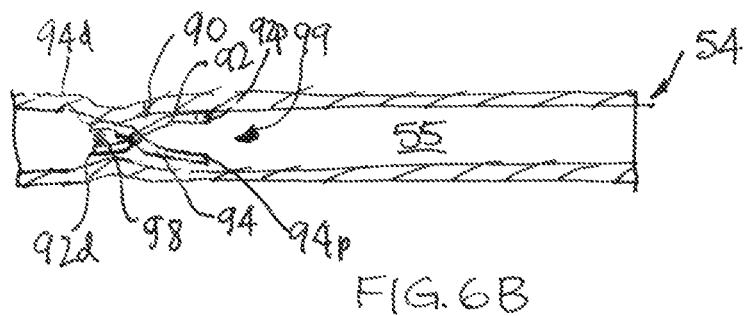

FIGS. 6A and 6B illustrate a variation of the embodiment of the guide wire extender 50 shown in FIG. 5, in which a clamp 90 is disposed within a portion of the receptacle 55. The embodiment of the clamp 90 depicted by FIGS. 6A and 6B includes at least two clamping elements 92 and 94 and a hinge 96 that secures the clamping elements 92 and 94 to one another, with a distal end 91 of the clamp 90 located on one side of the hinge 96 (the left side in FIGS. 6A and 6B) and a proximal end 99 of the clamp 90 located on an opposite side of the hinge (the right side in FIGS. 6A and 6B).

FIG. 6A shows the clamp 90 in a closed configuration. In the closed configuration, the ends of the clamping elements 92 and 94 at the proximal end 99 of the clamp 90 contact one another or are positioned very close to one another. In specific embodiments, when the clamp 90 is in its closed configuration the most distal ends of distal portions 92d and 94d of the clamping elements 92 and 94 may be spaced up to about 0.040 inch (e.g., 0.040 inch, 0.037 inch, 0.035 inch, 0.030 inch, etc.) apart from one another, while the most proximal ends of proximal portions 92p and 94p of the clamping elements 92 and 94 may be spaced less than about 0.010 inch (e.g. 0.009 inch, 0.005 inch, 0.000 inch, etc.) apart from each other.

FIG. 6B depicts the clamp 90 in an open configuration, in which the ends of the clamping elements 92 and 94 at the proximal end 99 of the clamp 90 are spaced apart from each other. In specific embodiments, when the clamp 90 is in its open configuration the most distal ends of the distal portions 92d and 94d may be spaced about 0.015 inch or more (e.g., 0.020 inch, 0.025 inch, etc.) apart from one, another, while the most proximal ends of proximal portions 92p and 94p of the clamping elements 92 and 94 may be spaced about 0.015 inch or more (e.g., 0.020 inch, 0.025 inch, etc.) apart from each other.

The clamp 90 may also include a spring 98. When the clamp 90 includes a spring 98, the spring 98 may be under greater tension when the clamp 90 is in its closed configuration (e.g., a relaxed configuration, etc.) than when the clamp 90 is in its open configuration (e.g., a stressed configuration, etc.). Thus, a spring 98 may urge the ends of the clamping elements 92 and 94 at the proximal end 99 of the clamp 90 toward one another, and against an element such as a wire that has forced the ends of the clamping elements 92 and 94 at the proximal end 99 of the clamp 90 apart from one another.

In use, a wire (not shown) may be introduced into the clamp 90 at its distal end 91, between the clamping elements 92 and 94. As the wire approaches the proximal side of the clamp 90, distal portions 92d and 94d of the clamping elements 92 and 94 may be forced together, which forces proximal portions 92p and 94p of the clamping elements 92 and 94 apart from one another. With the proximal portions 92p and 94p spaced apart from each other, and the clamp 90 at least partially open, enabling the wire to be pushed proximally through the entire length of the clamp 90. Once the wire has been pushed to a desired location, force against the distal portions 92d and 94d of the clamping elements 92 and 94 may be released, allowing them to move away from each other and the proximal portions 92p and 94p to move back toward one another (e.g., under the force of a spring 98, etc.). The proximal portions 92p and 94p may engage the wire and, thus, at least partially retain its longitudinal position relative within the receptacle 55 of the coupling element 54 of the guide wire extender 50 (FIG. 4).

Figure 7:
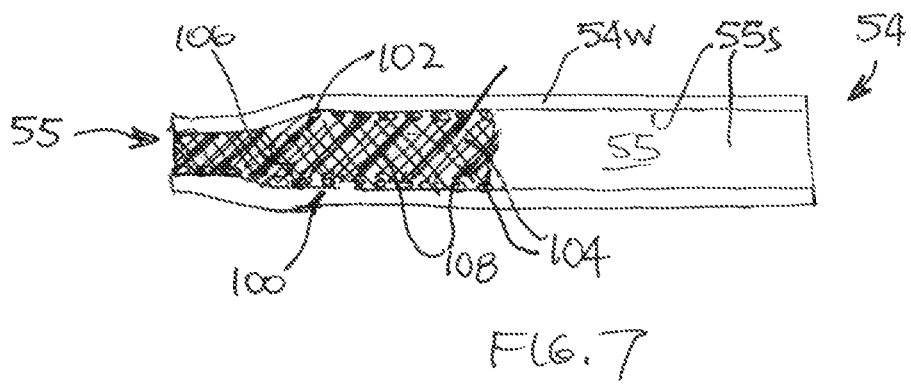
FIG. 7 depicts and embodiment of guide wire extender with a coupling element that includes a receptacle lined with a wire braid.

Referring now to FIG. 7, the coupling elements 54 of various embodiments of guide wire extenders 50 (FIG. 4) of the present invention may include wire braids 100 on the surfaces 55s of their receptacles 55. Such a wire braid 100 may comprise a tubular element with a wall 102 formed from braided wires 104 (e.g., wires with a rectangular cross-sectional shape, such as 0.001 inch thick by 0.003 inch wide, etc.). In some embodiments, the wire braid 100 may be partially embedded within a wall 54w of the coupling element 54 and exposed to or protrude from the surface 55s of the receptacle 55 of the coupling element 54. In other embodiments, the wire braid 100 may be positioned adjacent to the surface

55s of the receptacle 55. The wire braid 100 may have any configuration that will provide friction against a sire (not shown) positioned within the receptacle 55 and, thus, at least partially longitudinally retain the wire in position within the receptacle 55 and, thus, with respect to the coupling element 54 of the guide wire extender 50. An inner surface 106 of the wire braid 100 may include friction-enhancing features 108 (e.g., a helical thread, protrusions, ribs, etc.), which may be configured to increase the potential friction a wire braid 100 against a wire.

Although FIG. 7 illustrates a tapered wire braid 100 that lines a tapered receptacle 55, guide wire extenders 50 that include coupling elements 54 with wire braids 100 that have constant inner diameters are also within the scope of the present invention, as are guide wire extenders 50 that include coupling elements 54 with wire braids 100 that line receptacles 55 with constant inner diameters.

Regardless of the shape and/or dimensions of a receptacle 55 of a coupling element 54 of the present invention, the outer cross-sectional shape and dimensions of a coupling element 54 may be constant or substantially constant along the entire length of the coupling element 54. As a non-limiting example, a coupling element 54 may have a uniform outer diameter of about 0.035 inch to about 0.050 inch (e.g., 0.040 inch, etc.). In some embodiments, such as that shown in FIG. 5, a guide wire extender 50 may have a consistent or a substantially consistent outer cross-sectional shape and dimensions along its entire length. Embodiments of guide wire extenders 50 may have outer diameters of up to about 0.050 inch.

Figure 8:
FIGS. 8-8B depict another embodiment of a coupling element, as well as a guide wire extender of which the coupling element is a part.
Figure 8A:
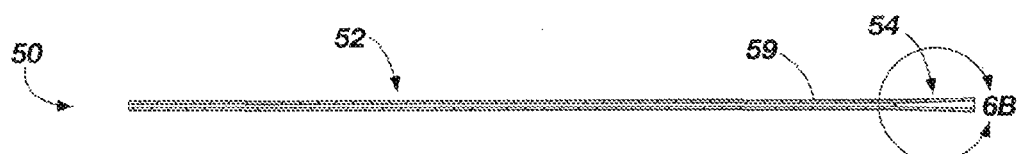

In other embodiments, the outer dimensions of the coupling element 54 may exceed corresponding outer dimensions of all or part of thew elongate extension 52. Such an embodiment is shown in FIGS. 8-8B, in which the outer surfaces of the coupling element 54 are tapered. As a non-limiting example, a tapered coupling element 54 may have an outer diameter of up to about 0.050 inch (e.g., about 0.030 inch to about 0.050 inch, about 0.040 inch, etc.) at its distal end and an outer diameter of about 0.018 inch at its proximal end. Such a taper may facilitate gripping of the coupling element 54 and, thus, enable a user to easily introduce the coupling element 54 onto the proximal portion 23 of a guide wire 20 (see, e.g., FIG. 4).

In embodiments where the coupling element 54 includes a receptacle 55, the receptacle may also extend into the elongate extension 52, or even completely through the length of the elongate extension 52.

Figure 9:
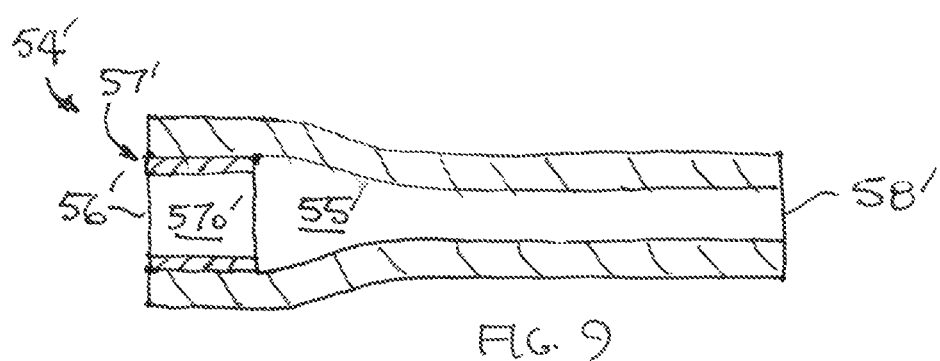

In FIG. 9, another embodiment of coupling element 54' is shown. The coupling element 54' is a somewhat elongated element. The coupling element 54' may be tubular, with a substantially uniform cross sectional shape and dimensions along its entire length. Thus, a receptacle 55' may extend from a proximal end 58' of the coupling element 54' to its distal opening 56'. In addition, the coupling element 54' may include an annular support 57' within a distal portion of the receptacle 55' (e.g., at the distal end 56' of the coupling element 54', etc.).

The manner in which the coupling element 54' engages a guide wire may be a function of the material for which the elongate medical instrument 54' is formed, the dimensions (e.g., diameter, etc.) of the receptacle 55' and optionally, other characteristics and features of the coupling element 54'. Without limiting the scope of the present invention, the coupling element 54' may be formed from a relatively sot, stretchable, elastic material (e.g., a polymer, etc.), such as a silicone. The dimensions of the receptacle 55' (e.g., its diameter, etc.) may be less than corresponding dimensions of a guide wire the coupling element 54' is designed to engage. Due to its relatively small dimensions, introduction of an appropriately sized guide wire into the receptacle 55' will cause the receptacle 55' to expand or otherwise deform. The stretchability of the material from which the coupling element 54' is formed will enable such expansion or deformation, while its elasticity and other characteristics will force the coupling; element 54' against the guide wire and cause it to engage the guide wire.

The annular support 57' may be oriented to maintain communication between the receptacle 55' and an exterior of the coupling element 54' through the distal end 56' of the coupling element 54'. An interference fit (e.g., the elasticity of the coupling element 54', etc.) may hold the annular support 57' in place within the receptacle 55'. Alternatively, or in addition, the annular support 57' may be secured in place within the receptacle by way of a suitable adhesive (e.g., glue, cement, epoxy, etc.).

The material from which the annular support 57' is formed may be more rigid than the material of the coupling element 54'. Without limitation, the annular support 57' may be formed from a polymer, a metal or any other suitable material. An opening 57o' through the annular support 57' may have dimensions (e.g. a diameter, etc.) that exceed corresponding dimensions of a guide wire with which the coupling element 54' is designed to be used. These features, may facilitate introduction of the guide wire into the receptacle 55' of the coupling element 54'.

As illustrated, due to its large outer diameter relative to the inner diameter of the coupling element 54' (i.e., the diameter of the receptacle 55'), the annular support 57' causes the receptacle 55' to tent and, thus, taper from a relatively large diameter at a location adjacent to (i.e., proximal to) the annular support 57' to its normal, relaxed diameter. As the guide wire is introduced into the opening 57o' of the annular support 57' and into the receptacle 55' through the distal end 56' of the coupling element 54', this tenting or tapering facilitates introduction of the guide wire into the smaller receptacle 55'.

In a specific embodiment, the coupling element 54' may have an outer diameter of about 0.035 inch and an inner diameter of about 0.010 inch. The annular support 57' may have an outer diameter of about 0.025 inch and an inner diameter of about 0.02.0 inch. Thus, when the annular support 57' resides within a distal portion of the receptacle 55', the annular support 57' may cause the inner diameter of the coupling element 54' and, thus, the diameter of the receptacle 55' at a location proximal to the annular support 57' to tent or taper from a diameter of about 0.025 inch to a diameter of about 0.010 inch.

In some embodiments, a coupling element 54' may include annular supports 57' within both a distal portion of its receptacle 55' and a proximal portion of its receptacle 55'.

A non-limiting embodiment of a method for manufacturing a coupling element 54 and an elongate extension 52 of a guide wire extender 50 from a polymer includes extruding a tubular element. In a specific embodiment, the tubular element may have an outer diameter of about 0.040 inch and an inner diameter of about 0.020 inch. The tubular element may have a length of about 150 cm. Once the tubular element has been formed, a core mandrel may be inserted into the lumen of the tubular element. A specific embodiment of such a core mandrel has a length of about 170 cm and an outer diameter of about 0.008 inch along all but a distal portion of its length. At the distal portion (e.g., about 10 cm of the length of the core mandrel, etc.), the outer diameter of the core mandrel tapers from about 0.008 inch to about 0.020 inch. With the core mandrel in the lumen of the tubular element, the material of the tubular element may be heat shrunk to conform to the shape of the core mandrel. In some embodiments, the core mandrel may include negative features that define engagement features on the interior surface of the receptacle 55 of the coupling element 54. The core mandrel may then be removed from the lumen of the newly formed coupling element 54.

Alternatively, the core mandrel may have a uniform outer diameter and, thus, define a portion of a coupling element 54 with a receptacle 55 that has a substantially uniform inner diameter. In some embodiments, a separately molded tapered section may be secured (e.g., welded, cemented, etc.) onto a distal end the heat-shrunk portion of the coupling element 54 to form a complete coupling element.

When a coupling element 54' includes one or more annular supports 57', as in the embodiment described in reference to FIG. 9, a variety of techniques may be suitable for manufacturing the coupling element 54'. By way of example and not by way of limitation, annular supports 57' may be inserted into open ends of a receptacle 55' after a coupling element 54' has been formed (e.g., by extrusion and cutting, molding, etc.). As another example, a coupling element 54' may be molded around one or more annular supports 57'.

With returned reference to FIG. 4, when disposed within the lumen 44 of the elongate medical instrument 40, the guide wire extender 50 may serve as a core or stylet of the elongate medical instrument 40. In the depicted embodiment, where the elongate medical instrument 40 comprises an aspiration catheter, it may have a length of about 135 cm to about 145 cm, while the guide wire extender 50 is slightly longer; for example about 150 cm long.

In some embodiments, the assembled relationship between the elongate medical instrument 40 and the guide wire extender 50 may be established prior to providing the guide wire extender 50 and the elongate medical instrument 40 to a healthcare professional. The guide wire extender 50, which may have an outer diameter OD that is less than an inner diameter ID of the lumen 44 of the elongate medical instrument 40, is configured to be received by and positioned within the lumen 44.

As illustrated, a length of the guide wire extender 50 may be at least as long as, and even exceed, a length of the elongate medical instrument 40. Such a length enables the elongate extension 52 of the guide wire extender 50 to extend through the entire length of the lumen 44 of the elongate medical instrument 40. The coupling element 54 at the distal end 51 of the guide wire extender 50 may protrude beyond a distal end 47 of the elongate medical instrument 40. A proximal portion 53 of the elongate extension 52 may also extend a sufficient distance beyond a proximal end 49 of the elongate medical instrument 40 to enable a user to hold the guide wire extender 50 and a guide wire 20 coupled thereto longitudinally in place as the elongate medical instrument 40 is introduced into the body of a subject.

Figure 10:
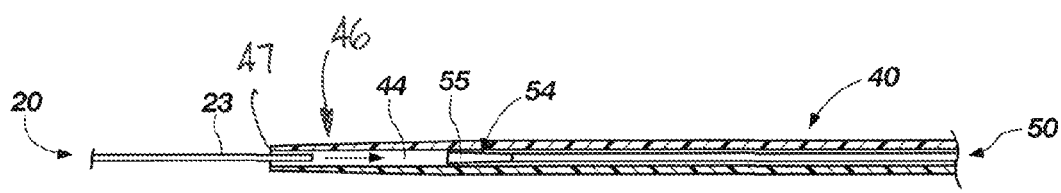
FIG. 10 illustrates an embodiment of coupling element with an annular, support at a distal end to facilitate insertion of a guide wire into the coupling element.

In other embodiments, including, but not limited to, that illustrated by FIG. 10, the coupling element 54 of the guide wire extender 50 does not protrude beyond the distal end 47 of the elongate medical instrument 40. Instead, the coupling element 54 may be seated within the lumen 44 of the elongate medical instrument 40. In a more particular embodiment, the coupling element 54 may be temporarily secured within the lumen 44.

While the coupling element 54 is seated within the lumen 44, the proximal portion 23 of a guide wire 20 may be introduced into the lumen 44 through the distal end 47 of the elongate medical instrument 40, then into a receptacle 55 of the coupling element 54. Once the proximal portion 23 of the guide wire 20 is secured within the receptacle of the coupling element 54, the elongate medical instrument 40 may be pushed distally over the guide wire 20 and, thus, introduced into the body of a subject.

Such an arrangement may, without limiting the scope of the present invention, be used to introduce elongate medical instruments 40 (e.g., catheters, etc.) with small (e.g., 0.025 inch, 0.030 inch, etc.) distal tips, or crossing profiles, to be introduced into the body of a subject along a relative short (e.g., 180 cm, etc.) guide wire 20 without the requirement of rapid exchange features. FIG. 10 depicts such an embodiment of elongate medical instrument 40. Specifically, a distal portion 46 (e.g., having a length of about 10 cm to about 40 cm, etc.) of the elongate medical instrument 40 may be tapered, with its outer diameter increasing (e.g., from about 0.025 inch, etc.) from its distal end 47 to a more proximal location (e.g., to about 0.045 inch, etc.).

As depicted in FIG. 4, the assembly 60 may be coiled, which enables a single user to couple the guide wire extender 50 to the proximal end 22 of a guide wire 20 and introduce the elongate medical instrument 40 into the body of a subject, along the guide wire 20, without a substantial risk of contaminating the guide wire extender 50 or the elongate medical instrument 40. The assembly 60 may be coiled in such a way that the distal end 51 and the proximal portion 53 of the elongate extension 52 of the guide wire extender 50 are close to one another, enabling a user's hand that holds the proximal portion 53 of the elongate extension 52 of the guide wire extender 50 to remain in close proximity to his or her other hand as the other hand introduces the elongate medical instrument 40 into the body of the subject.

Figure 11:
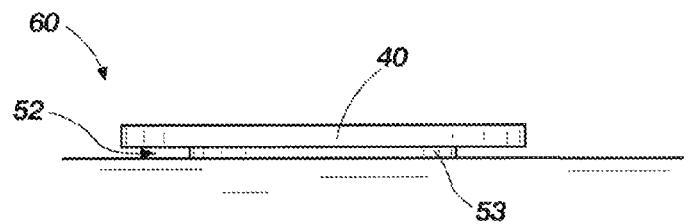
FIG. 11 illustrates an embodiment of assembly in which a guide wire extender is coiled in two or more planes.

In some embodiments, such as that depicted by FIG. 11, an assembly 60 may be coiled in such a way that the proximal portion 53 of the elongate extension 52 and the remainder of the elongate extension 52 are located in different planes. In such an embodiment, the proximal portion 53, which extends beyond the proximal end 49 (see e.g., FIG. 4) of the elongate medical instrument 40, may rest on a surface, such as a tabletop or a sterile drape, while the remainder of the elongate extension 52 is elevated above and, thus, out of contact with the surface. While the remainder of the elongate extension 52 remains out of contact with the surface on which the proximal portion 53 rests, the elongate medical instrument 40 also remains out of contact with the surface, minimizing the probability that the elongate medical instrument 40 will be contaminated.

Figure 12:
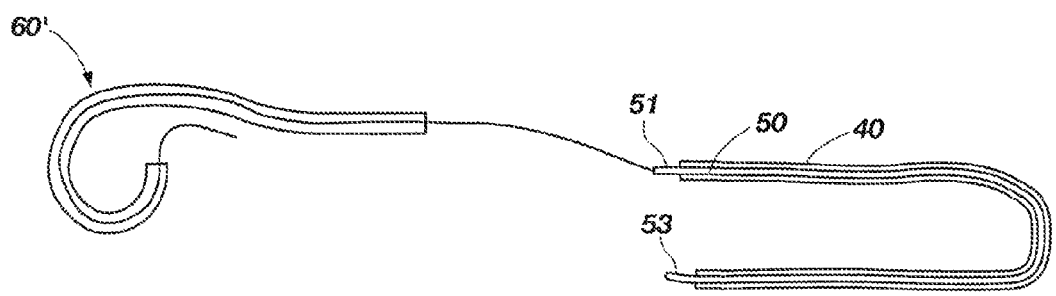
FIG. 12 depicts another embodiment of an assembly including an elongate medical instrument and a guide wire extender therein.

FIG. 12 illustrates another embodiment of assembly 60', in which the elongate medical instrument 40 and the guide wire extender 50 therein are set in a simple curve that positions the distal end 51 and the proximal portion 53 of the elongate extension 52 of the guide wire extender 50 in close proximity to one another. The simple curve effectively decreases the length of the assembly 60' by more than half, increasing a user's ability to control the assembly 60' while reducing the likelihood that the elongate medical instrument 40 and/or the guide wire extender 50 will contact a potentially contaminating surface, such as the floor.

In use, a guide wire extender 50 enables elongate medical instruments 40 that lack rapid exchange capabilities to be introduced into the bodies of subjects over the short (e.g., 180 cm, etc.) guide wires 20 that are typically used in rapid exchange systems. For example, and not by way of limitation, a guide wire extender 50 of the present invention enables the introduction of an aspiration catheter having a length of about 135 cm to about 145 cm, an outer diameter of about 0.060 inch to about 0.068 inch, and an inner diameter of about 0.050 inch to about 0.058 inch into the body of a subject over a 180 cm long standard guide wire. By eliminating the requirement of rapid exchange features, the lumen size of the aspiration catheter and, thus, its ability to aspirate, may be optimized.

Figure 13:
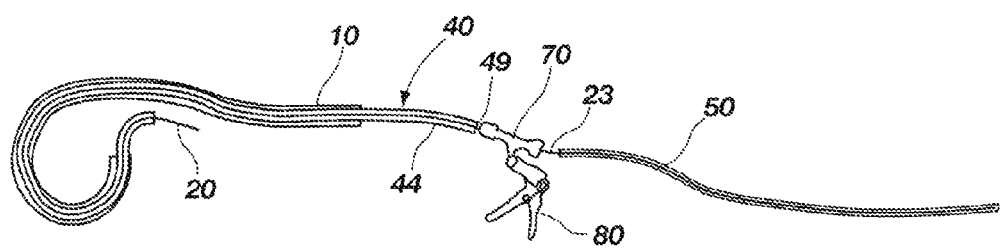
FIG. 13 shows a system that includes a guide wire, an elongate medical instrument, a guide wire extender, a connector, and another medical device in communication with the elongate medical instrument through the connector.

With reference now turned to FIG. 13, when the introduction of an elongate medical instrument 40 comprising an aspiration catheter into an optional guide catheter 10 and into the body of a subject has been completed, a connector 70 (e.g., the depicted Y adapter, a T adapter, etc.) may be introduced over the guide wire extender 50 and secured to the proximal end 49 of the elongate medical instrument 40 and over the proximal portion 23 of the guide wire 20 in a manner known in the art to establish communication with the lumen 44 of the elongate medical instrument 40. In some embodiments, the guide wire 20 may remain in place within the lumen 44, and the guide wire extender 50 may continue to be coupled to the guide wire 20. With the connector 70 in place, an aspiration device 80, such as the depicted aspiration syringe, may be coupled to the connector, then used to aspirate material from the body of the subject, through the elongate medical instrument 40.

Of course, in embodiments where the elongate medical instrument 40 is used to perform other medical procedures, other appropriate equipment (e.g., injection or infusion equipment, etc.) may be coupled to the connector 70. Other examples of elongate medical instruments with which a guide wire extender 50 of the present invention may be used include, without limitation, crossing catheters, support catheters and distal access catheters.

Although the foregoing description contains many specifics, these should not be construed as limiting the scope of the invention or of any of the appended claims, but merely as providing information pertinent to some specific embodiments that may fall within the scopes of the invention and the appended claims. Other embodiments of the invention may also be devised which lie, within the scopes of the invention and the appended claims. Features from different embodiments may be employed in combination. The scope of the invention is, therefore, indicated and limited only by the appended claims and their legal equivalents. All additions, deletions and modifications to the invention, as disclosed herein, that fall within the meaning and scopes of the claims are to be embraced thereby.

What is claimed:

1. A method for introducing an elongate medical instrument into a body of a subject, comprising:
   introducing a distal end of a guide wire into a body of a subject, with an opposite, proximal end of the guide wire remaining outside of the body of the subject;
   introducing the proximal end of the guide wire into a distal end of a lumen of a catheter and into contact with a distal end of an extension wire that resides within the lumen of the catheter, wherein the distal end of the extension wire resides within the lumen of the catheter prior to contact with the promixal end of the guide wire, and wherein the lumen of the catheter guides the proximal end of the guide wire into contact with the distal end of the extension wire to couple the proximal end of the guide wire with the distal end of the extension wire; and
   moving the catheter distally over the extension wire and the guide wire to introduce the catheter into the body of the subject.

2. The method of claim 1, further comprising:
   holding a proximal end of the extension wire while moving the catheter.

3. The method of claim 2, wherein holding and moving are effected by the same person.

4. The method of claim 1, wherein the distal end of the extension wire and the proximal end of the guide wire are coupled as a proximal end of the extension wire protrudes from a proximal end of the catheter.

5. A method for introducing an elongate medical instrument into a body of a subject, comprising:
   introducing a distal end of a guide wire into a body of a subject, with an opposite, proximal end of the guide wire remaining outside of the body of the subject;
   providing a catheter and an extension wire, a distal end of the extension wire residing within a lumen of the catheter; and
   after providing the catheter and the extension wire with the distal end of the extension wire residing within the lumen of the catheter, introducing the proximal end of the guide wire into a distal end of the lumen of the catheter and into contact with the distal end of the extension wire, the lumen of the catheter guiding the proximal end of the guide wire into contact with the distal end of the extension wire to enable coupling of the proximal end of the guide wire with the distal end of the extension wire.

6. The method of claim 5, wherein introducing the distal end of the guide wire into the body of the subject occurs before introducing the proximal end of the guide wire into the distal end of the lumen of the catheter.

7. A method for introducing an elongate medical instrument into a body of a subject, comprising:
   introducing a distal end of a guide wire into a body of a subject, with an opposite, proximal end of the guide wire remaining outside of the body of the subject;
   providing a catheter and an extension wire, a distal end of the extension wire residing within a lumen of the catheter;
   after providing the catheter and the extension wire with the distal end of the extension wire residing within the lumen of the catheter, introducing the proximal end of the guide wire into a distal end of the lumen of the catheter and into contact with the distal end of the extension wire, the lumen of the catheter guiding the proximal end of the guide wire into contact with the distal end of the extension wire to enable coupling of the proximal end of the guide wire with the distal end of the extension wire; and
   moving the catheter distally over the extension wire and the guide wire to introduce the catheter into the body of the subject.

8. The method of claim 7, further comprising:
   holding a proximal end of the extension wire while moving the catheter.

9. The method of claim 8, wherein holding and moving are effected by the same person.

10. The method of claim 7, wherein introducing the proximal end of the guide wire into the distal end of the lumen of the catheter occurs while a proximal end of the extension wire protrudes from a proximal end of the catheter.

11. The method of claim 7, wherein providing the catheter and the extension wire comprises providing the catheter and the extension wire with a proximal end of the extension wire protruding from a proximal end of the catheter.

12. The method of claim 11, further comprising:
   holding the proximal end of the extension wire; and
   moving the catheter distally over the extension wire and the guide wire while holding the proximal end of the extension wire to introduce the catheter into the body of the subject.

13. The method of claim 12, wherein holding and moving are effected by the same person.

14. The method of claim 11, wherein introducing the proximal end of the guide wire into the distal end of the lumen of the catheter occurs while the proximal end of the extension wire protrudes from the proximal end of the catheter.

* * * * *